(12) United States Patent
Fujita et al.

(10) Patent No.: US 11,291,375 B2
(45) Date of Patent: Apr. 5, 2022

(54) PULSE WAVE DETECTOR AND BIOMETRIC INFORMATION MEASUREMENT DEVICE

(71) Applicant: OMRON HEALTHCARE CO., LTD., Kyoto (JP)

(72) Inventors: Reiji Fujita, Muko (JP); Masayuki Fukutsuka, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 505 days.

(21) Appl. No.: 16/158,417

(22) Filed: Oct. 12, 2018

(65) Prior Publication Data

US 2019/0038153 A1 Feb. 7, 2019

Related U.S. Application Data

(63) Continuation of application No. PCT/JP2017/014750, filed on Apr. 11, 2017.

(30) Foreign Application Priority Data

Apr. 15, 2016 (JP) .............................. JP2016-081951

(51) Int. Cl.
*A61B 5/021* (2006.01)
*A61B 5/0225* (2006.01)
(Continued)

(52) U.S. Cl.
CPC ............ *A61B 5/02108* (2013.01); *A61B 5/02* (2013.01); *A61B 5/0225* (2013.01); *A61B 5/681* (2013.01)

(58) Field of Classification Search
CPC ... A61B 5/0225; A61B 5/02108; A61B 5/681; A61B 5/6824; A61B 5/6843;
(Continued)

(56) References Cited

U.S. PATENT DOCUMENTS 4,784,152 A 11/1988 Shinoda et al.
2011/0275915 A1 11/2011 Allgeyer
(Continued)

FOREIGN PATENT DOCUMENTS

CN 202313298 7/2012
EP 0 289 700 11/1988
(Continued)

OTHER PUBLICATIONS

Norio Kawamura; Takehito Fukunaga, English Translation of "Device for detecting pulse waves", Apr. 26, 1994, Japanese Patent Office, Translation obtained from Japan Platform for Patent Information (Year: 1994).*

(Continued)

*Primary Examiner* — Navin Natnithithadha
(74) *Attorney, Agent, or Firm* — Wenderoth, Lind & Ponack, L.L.P.

(57) ABSTRACT

A pulse wave detector includes a pulse wave detection sensor which is configured to detect a pressure pulse wave from an artery of a measurement subject, a pressing member which supports the pulse wave detection sensor and is configured to be moved in one direction to press the pulse wave detection sensor against a body surface of the measurement subject, a plurality of guiding members which are placed around the pulse wave detection sensor in a plan view as seen in the one direction and extend in the one direction, and a supporting member which supports the plurality of guiding members. The pressing member includes pass-through portions through which the plurality of guiding members are passed to be movable along the guiding members, respectively.

8 Claims, 7 Drawing Sheets

(51) Int. Cl.
    *A61B 5/02*     (2006.01)
    *A61B 5/00*     (2006.01)

(58) Field of Classification Search
    CPC ... A61B 5/022; A61B 5/02; A61B 2562/0247; A61B 2562/043; A61B 5/02438; A61B 5/0295
    See application file for complete search history.

(56) References Cited

U.S. PATENT DOCUMENTS

| | | | | |
|---|---|---|---|---|
| 2016/0157741 | A1* | 6/2016 | Chen | G01J 5/0896 600/479 |
| 2017/0224226 | A1* | 8/2017 | Kitagawa | A61B 5/11 |
| 2017/0367649 | A1 | 12/2017 | Kitagawa et al. | |

FOREIGN PATENT DOCUMENTS

| | | |
|---|---|---|
| EP | 0 823 238 | 2/1998 |
| JP | 1-288228 | 11/1989 |
| JP | 06-031702 | 4/1994 |
| JP | H0631702 U * | 4/1994 |
| JP | 7-039802 | 7/1995 |
| JP | 10-43150 | 2/1998 |
| JP | 2000-41960 | 2/2000 |
| JP | 2002-330932 | 11/2002 |
| JP | 2004-16744 | 1/2004 |
| JP | 2005-342163 | 12/2005 |
| JP | 2009-28057 | 2/2009 |
| JP | 2010-136941 | 6/2010 |
| JP | 2010-220949 | 10/2010 |
| JP | 2016-158767 | 9/2016 |

OTHER PUBLICATIONS

Office Action dated May 7, 2020 in corresponding Japanese Patent Application No. 2016-081951 with English-language translation.
Office Action dated Sep. 14, 2020 in corresponding Chinese Patent Application No. 201780023368.1 with English-language translation.
Extended European Search Report dated Oct. 23, 2019 in corresponding European Patent Application No. 17782372.1.
International Search Report dated Jul. 4, 2017 in International (PCT) Application No. PCT/JP2017/014750.
Written Opinion of the International Searching Authority dated Jul. 4, 2017 in International Application No. (PCT) PCT/JP2017/014750.

* cited by examiner

PULSE WAVE DETECTOR AND BIOMETRIC INFORMATION MEASUREMENT DEVICE

CROSS-REFERENCE TO RELATED APPLICATIONS

This is a Continuation of International Patent Application No. PCT/JP2017/014750 filed Apr. 11, 2017, which claims the benefit of Japanese Patent Application No. 2016-081951 filed Apr. 15, 2016. The disclosures of the prior applications are hereby incorporated by reference herein in their entireties.

TECHNICAL FIELD

Aspects of the present invention relate to a pulse wave detector and a biometric information measurement device.

BACKGROUND ART

A biometric information measurement device is known that, in a state where a pulse wave detection sensor for detecting a pulse wave is directly contacted with a living body portion through which an artery such as the radial artery in the wrist passes, can measure biometric information such as the heart rate, the pulse rate, or the blood pressure by using information detected by the pulse wave detection sensor (see Patent Literature 1 (JP-A-H1-288228)).

The biometric information measurement device disclosed in Patent Literature 1 has a pressing mechanism which moves the pulse wave detection sensor in one direction by supplying a fluid such as the air, thereby pressing the pulse wave detection sensor against the body surface.

The pressing mechanism has a plate-like member which is slidably fitted to a guide rod that is disposed above the middle of a detection surface of the pulse wave detection sensor, and that extends in the above-described one direction. The pulse wave detection sensor is fixed to a flat surface of the plate-like member.

When the plate-like member is moved along the guide rod, the detection surface of the pulse wave detection sensor can be pressed against the body surface while maintaining the detection surface at a state where the surface is approximately parallel.

In order to accurately detect a pulse wave which is necessary in calculation of biometric information, it is required to press a detection surface of a pulse wave detection sensor against the body surface at a stabilized pressure.

The biometric information measurement device disclosed in Patent Literature 1 has the configuration where the plate-like member is moved along the one guide rod which is disposed above the middle of the detection surface.

If a stress is concentrated in the circumference of the plate-like member, the stability of the detection surface is lowered, so that it is difficult to uniformly press the detection surface against the body surface at a stabilized pressure.

SUMMARY

Embodiments of the present invention address the above disadvantages and other disadvantages not described above. However, the present invention is not required to overcome the disadvantages described above, and thus, an exemplary embodiment of the present invention may not overcome any of the problems described above.

A pulse wave detector according to an embodiment of the present invention includes: a pulse wave detection sensor which is configured to detect a pressure pulse wave from an artery of a measurement subject; a pressing member which supports the pulse wave detection sensor and is configured to be moved in one direction to press the pulse wave detection sensor against a body surface of the measurement subject; a plurality of guiding members which are placed around the pulse wave detection sensor in a plan view as seen in the one direction and extend in the one direction; and a supporting member which supports the plurality of guiding members, wherein the pressing member includes pass-through portions through which the plurality of guiding members are passed to be movable along the guiding members, respectively.

A biometric information measurement device according to an embodiment of the present invention includes: the above pulse wave detector; and a biometric information calculating section which is configured to calculate biometric information based on the pulse wave detected by the pulse wave detection sensor.

BRIEF DESCRIPTION OF DRAWINGS

The above and other aspects of the present invention will become more apparent and more readily appreciated from the following description of embodiments of the present invention taken in conjunction with the attached drawings.

DESCRIPTION OF EMBODIMENTS

Hereinafter, embodiments of the present invention will be described with reference to the drawings.

Figure 1:
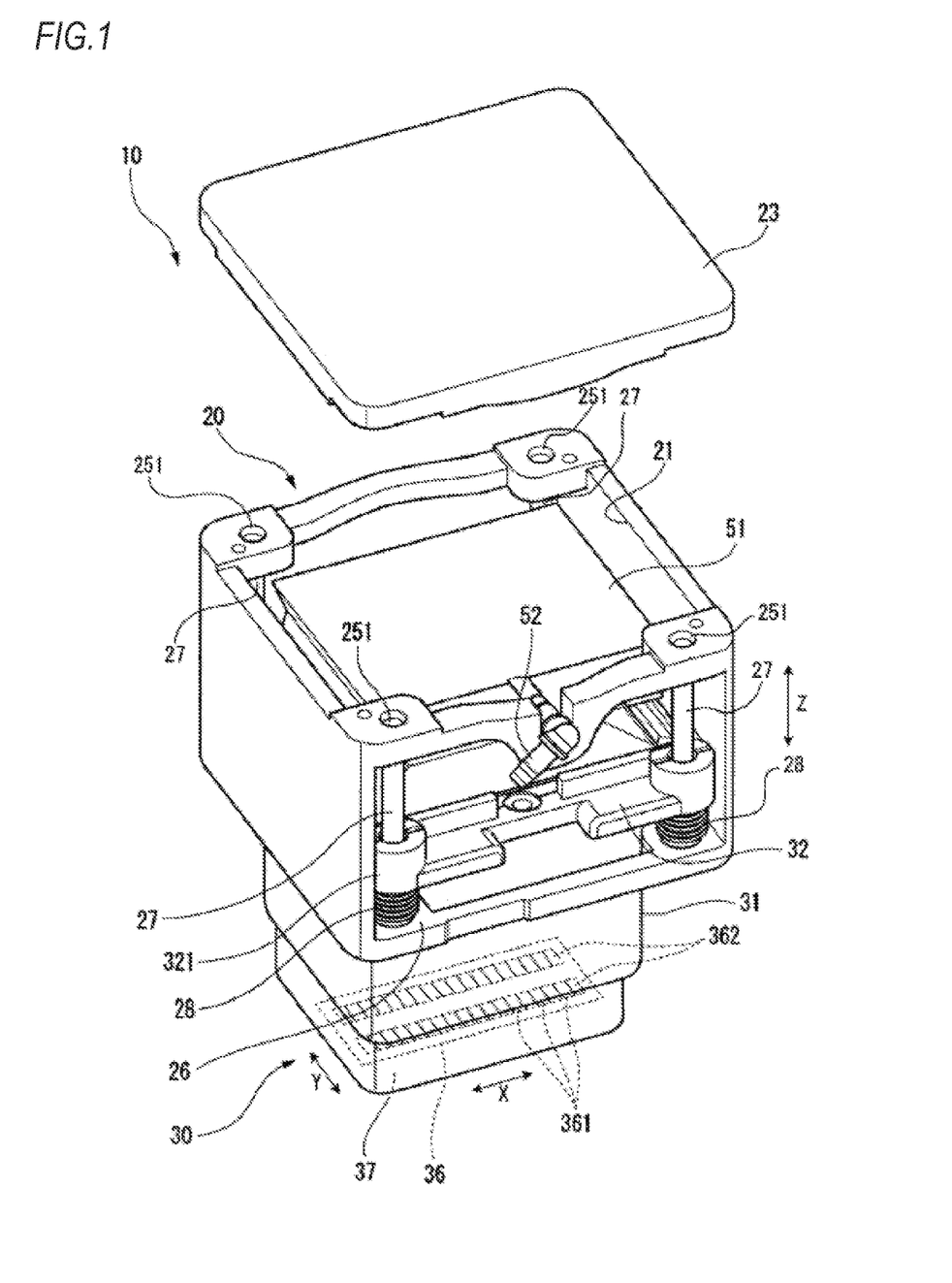
FIG. 1 is a perspective view schematically showing the configuration of a pulse wave detector 10 which is an embodiment of the present invention.
Figure 2:
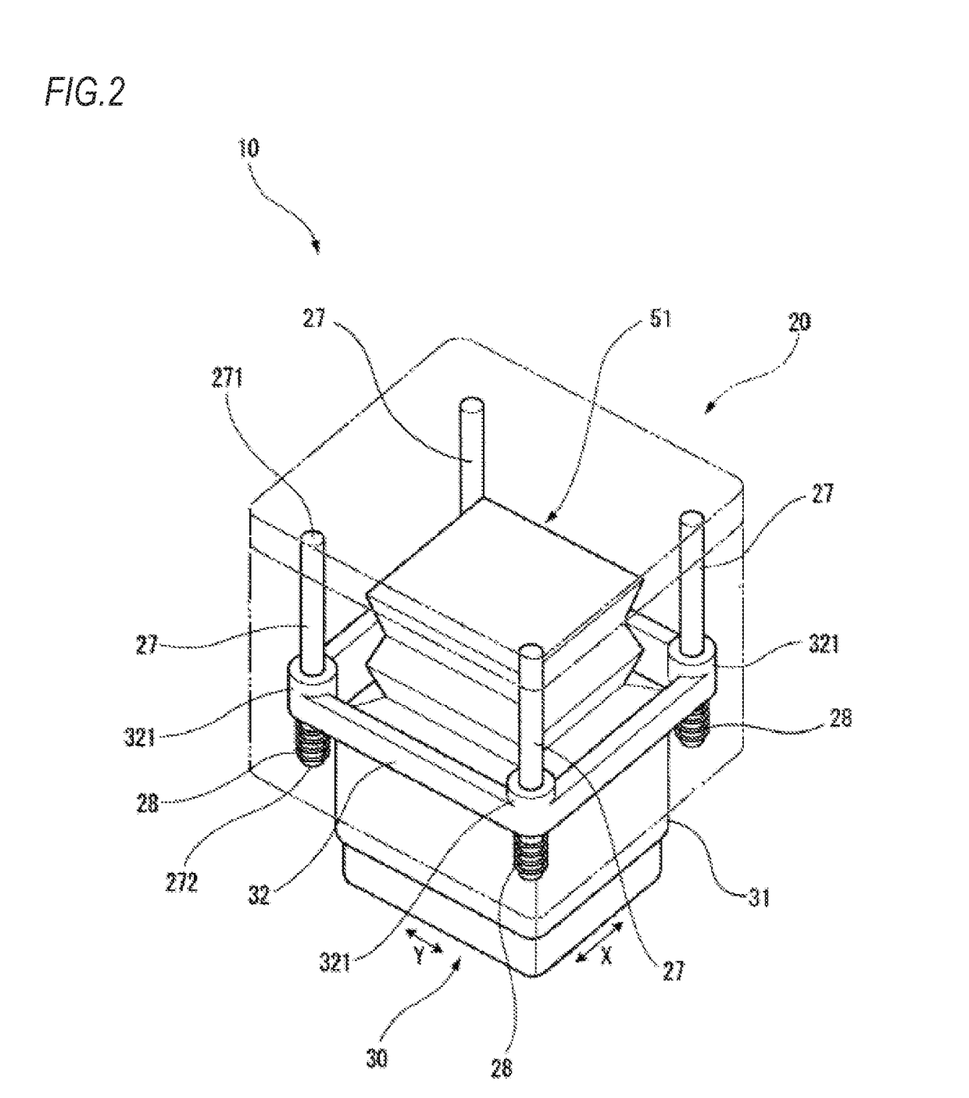
FIG. 2 is a perspective view schematically showing the internal configuration of a housing 20 of the pulse wave detector 10 shown in FIG. 1.
Figure 3:
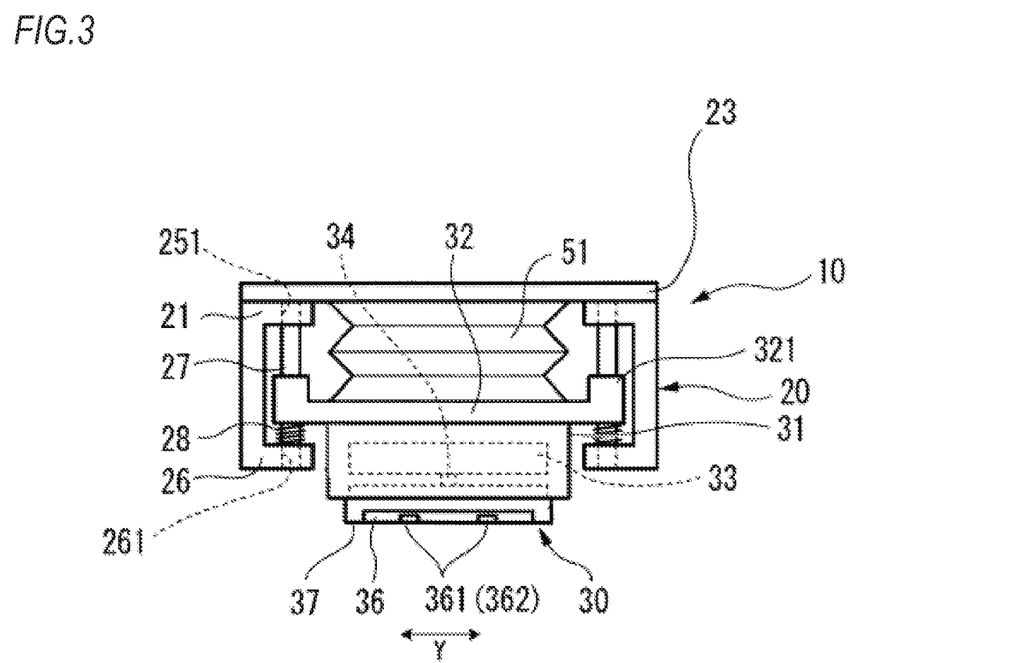
FIG. 3 is a sectional diagram of the pulse wave detector 10 shown in FIG. 1, taken in the direction Y.

FIG. 1 is a perspective view schematically showing the configuration of a pulse wave detector 10 which is an embodiment of the present invention. FIG. 2 is a perspective view schematically showing the internal configuration of a housing 20 of the pulse wave detector 10 shown in FIG. 1. FIG. 3 is a sectional diagram of the pulse wave detector 10 shown in FIG. 1, taken in the direction Y.

The pulse wave detector 10 is accommodated in a housing (not shown), and used while the housing is attached to a living body portion (for example, the wrist) through which an artery (for example, the radial artery) from which the pulse wave of the measurement subject is to be detected passes, by a strip-like band or the like.

In the housing, a controller is incorporated which functions as the biometric information calculating section that calculates biometric information such as the heart rate, the pulse rate, or the blood pressure based on the pulse wave detected by the pulse wave detector 10, and that stores the information. The biometric information measurement device is configured by the biometric information calculating section and the pulse wave detector 10.

As shown in FIG. 1, the pulse wave detector 10 has the housing 20 having a hollow portion. Although, in the example of FIGS. 1 to 3, the housing 20 has a rectangular tubular shape, the housing may have another shape such as a cylindrical shape. In the housing 20, a lid member 23 for closing the opening of the end surface is disposed, and FIG. 1 shows a state where the lid member 23 is detached.

The pulse wave detector 10 further includes: four guide pins 27 which are supported by the housing 20; four springs 28 through which the four guide pins 27 are passed respectively; a pressing member 32 which can be moved in the direction Z that is the one direction, while being guided by the four guide pins 27; an air bag 51 which is fixed to the front surface of the pressing member 32; a rotation driving section 31 which is fixed to the rear surface of the pressing member 32; and a pulse wave detection sensor 30 which is supported by the rotation driving section 31.

Each of the guide pins 27 is the rod-like guiding member which extends in the direction Z. Although, in the example of FIGS. 1 to 3, the shape of the guide pin 27 is a columnar shape, the guide pin may have another shape such as a square prism or a triangular prism. The guide member has a structure which is configured, when a plane having an arbitrary shape is moved in the one direction, by the locus of the plane.

Upper end portions 271 (see FIG. 2) in the direction Z of the guide pins 27 are fitted into hole portions 251 which are disposed in an upper end portion 21 in the direction Z of the housing 20, respectively (see FIGS. 1 and 3).

Lower end portions 272 (see FIG. 2) in the direction Z of the guide pins 27 are fitted into hole portions 261 (see FIG. 3) which are disposed in a lower end portion 26 in the direction Z of the housing 20, respectively.

According to the configuration, the four guide pins 27 are supported by the housing 20. The housing 20 constitutes the supporting member which supports the four guide pins 27. The hole portions 251 and the hole portions 261 constitute the fitting portions.

The front and rear surfaces of the pressing member 32 are planes which are perpendicular to the direction Z, respectively.

Four slide portions 321 are formed on the front surface of the pressing member 32. Each of the slide portions 321 has a hollow portion which is formed by a locus of a plane having a shape that is identical with the plan-view shape in the direction Z of each of the guide pins 27. The locus is produced when the plane is moved in the direction Z. The guide pins 27 are passed through the hollow portions, respectively.

In the example of FIGS. 1 to 3, the guide pins 27 have a columnar shape, and therefore the slide portions 321 have a cylindrical shape. The slide portions 321 constitute the pass-through portions through which the guide pins 27 are passed in a manner that the portions are movable along the guide pins 27 in the direction Z.

The bellows-like air bag 51 is fixed in a region which is surrounded by the four slide portions 321 in the front surface of the pressing member 32. A pipe 52 communicates with the air bag 51 (see FIG. 1). The pressure in the air bag 51 is controlled by a pump (not shown) through the pipe 52.

The surface of the air bag 51 which is opposite to the surface on the side of the pressing member 32 is fixed to the lid member 23 of the housing 20. Therefore, the air bag 51 inflates with an increase of the internal pressure toward the side opposite to the lid member 23 to move the pressing member 32 in the direction Z.

The air bag 51 is used for moving the pressing member 32 in the direction Z by means of an air pressure. A configuration where the pressing member 32 is moved in the direction Z by an actuator may be employed in place of the air bag 51.

Each of the springs 28 is placed between the pressing member 32 and the lower end portion 26 of the housing 20. One end of the spring is fixed to the pressing member 32, and the other end to the lower end portion 26. The springs 28 are urging members for urging the pressing member 32 toward the air bag 51.

Figure 4:
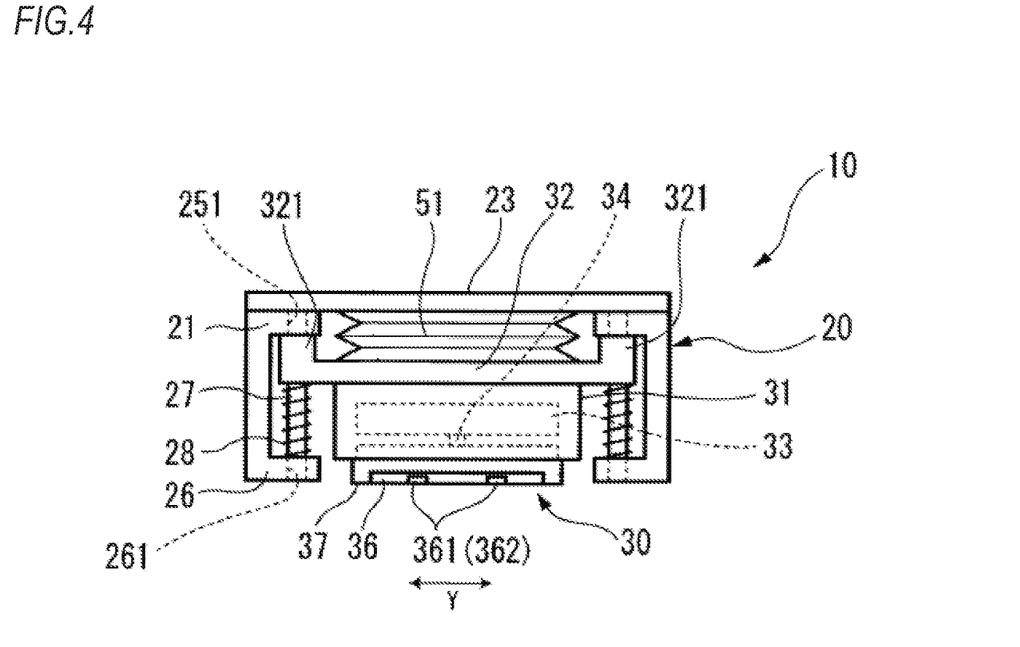
FIG. 4 is a diagram showing a state where the internal pressure of an air bag 51 in the state shown in FIG. 3 is reduced.

FIG. 4 is a diagram showing a state where the internal pressure of the air bag 51 in the state shown in FIG. 3 is reduced. In this state, the pressing member 32 is moved toward the upper end portion 21 of the housing 20 by the urging forces of the springs 28.

The pulse wave detection sensor 30 is a sensor for detecting a pressure oscillation wave (pressure pulse wave) that propagates from the artery in the living body portion to which the pulse wave detector 10 is attached, to the body surface of the living body portion.

In the example of FIG. 1, the pulse wave detection sensor 30 includes a sensor chip 36 in which a plurality (two in the example of FIG. 1) of element rows 362 each configured by a plurality of pressure detecting elements 361 that are arranged in the direction X.

The plurality of element rows 362 are arranged in the direction Y which is perpendicular to the direction X. As the pressure detecting elements 361, for example, elements of the strain gauge type, the semiconductor piezoresistance type, or the static capacitance type are used. The direction X and the direction Y are directions perpendicular to the direction Z.

The pressure detecting elements 361 disposed in the pulse wave detection sensor 30 are formed on the same plane, and the plane is protected by a protecting member such as a resin.

The plane on which the pressure detecting elements 361 are formed, and the front surface of the protecting member which protects the plane are parallel to each other, and the front surface of the protecting member constitutes a detection surface 37 (see FIG. 3). In the example of FIGS. 1 to 3, the size of the detection surface 37 in the plan view as seen in the direction Z coincides with that of the pulse wave detection sensor 30.

The rotation driving section 31 is fixed to the rear surface of the pressing member 32, whereby the section is supported by the pressing member 32.

The rotation driving section 31 includes: a rotating mechanism 34 which, while setting a state where the detection surface 37 of the pulse wave detection sensor 30 is perpendicular to the direction Z, as a reference, rotates the detection surface 37 of the pulse wave detection sensor 30 about each of two axes (an axis extending in the direction X, and an axis extending in the direction Y) that are perpendicular to the direction Z and to each other; and an actuator 33 which drives the rotating mechanism 34 (see FIG. 3).

The pulse wave detection sensor 30 is rotatably supported by the rotation driving section 31, and a state where the detection surface 37 is perpendicular to the direction Z is set as the steady state. The pulse wave detection sensor 30 is supported by the rotation driving section 31, and the rotation driving section 31 is supported by the pressing member 32. That is, the pressing member 32 is a member for supporting the pulse wave detection sensor 30.

Figure 5:
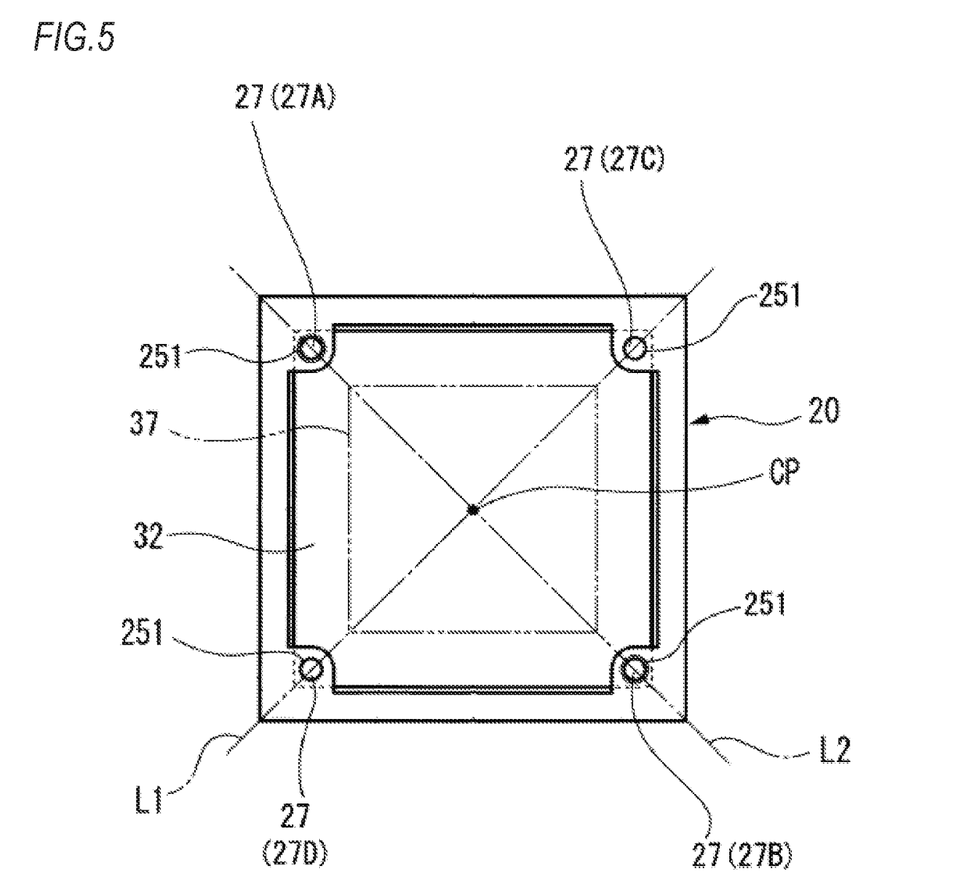
FIG. 5 is a plan view of of the pulse wave detector 10 shown in FIG. 1, as seen in the direction Z.

FIG. 5 is a plan view of of the pulse wave detector 10 shown in FIG. 1, as seen in the direction Z. In FIG. 5, illustration of the lid member 23, the air bag 51, and the pipe 52 is omitted.

As shown in FIG. 5, the four guide pins 27 which are disposed in the four corners (edge portions) of the housing 20 are placed around the pulse wave detection sensor 30. The four guide pins 27 are classified into a pair of guide pins 27A and 27B which are arranged across the detection surface 37 of the pulse wave detection sensor 30, and a pair of guide pins 27C and 27D which are arranged across the detection surface 37 of the pulse wave detection sensor 30.

A straight line L2 connecting the guide pins 27A and 27B passes through the center CP of the detection surface 37. A straight line L1 connecting the guide pins 27C and 27D passes through the center CP of the detection surface 37. The straight line L1 and the straight line L2 are perpendicular to each other. The center CP of the detection surface 37 may be the center of gravity of the detection surface 37.

Upper end portions 271 of the guide pins 27A and 27B are loose-fitted into the hole portions 251 of the housing 20, respectively.

Lower end portions 272 of the guide pins 27A and 27B are loose-fitted into the hole portions 261 of the housing 20, respectively.

Namely, the diameters of the guide pins 27A and 27B are slightly smaller than those of the hole portions 251 and 261.

By contrast, upper end portions 271 of the guide pins 27C and 27D are press-fitted into the hole portions 251 of the housing 20, respectively.

Lower end portions 272 of the guide pins 27C and 27D are press-fitted into the hole portions 261 of the housing 20, respectively.

Namely, the diameters of the guide pins 27C and 27D coincide with those of the hole portions 251 and 261.

The operation of the thus configured pulse wave detector 10 will be described. The pulse wave detector 10 is attached to the wrist so that the detection surface 37 is located above the radial artery, and the direction X intersects the radial artery.

When instructions for starting detection of a pulse wave is provided in this state, the controller controls the pump so as to raise the internal pressure of the air bag 51. When the internal pressure of the air bag 51 is raised, the air bag 51 inflates to cause the slide portions 321 of the pressing member 32 to move respectively along the four guide pins 27 in the direction Z, and the detection surface 37 of the pulse wave detection sensor 30 supported by the pressing member 32 is pressed against the body surface.

In the state where the detection surface 37 of the pulse wave detection sensor 30 is in contact with the body surface, the controller controls the rotation driving section 31 to adjust the rotation angle of the detection surface 37 about the direction X, and that of the detection surface 37 about the direction Y to respective optimum values so that the pulse wave detection accuracy is maximum.

Then, the controller holds the pressing force which is exerted by the pressing member 32 against the body surface in this state, to the optimum value, and detects a pressure pulse wave based on signals which are detected by the pressure detecting elements 361 of the pulse wave detection sensor 30. The controller calculates biometric information based on the detected pressure pulse wave, and causes the biometric information to be stored in a storage medium.

As described above, the pulse wave detector 10 has the configuration where the guide pins 27 are placed around the pulse wave detection sensor 30 in a plan view as seen in the direction Z, and the movement of the pressing member 32 is guided by the guide pins 27.

The existence of the plurality of guiding mechanisms enables the pulse wave detection sensor 30 which is supported by the pressing member 32, to be stably moved in the direction Z, and the detection surface 37 to be pressed against the body surface at a stabilized pressure.

Since the plurality of guide pins 27 are placed around the pulse wave detection sensor 30 as described above, it is possible to maintain the state where the front and rear surfaces of the pressing member 32 are perpendicular to the direction Z, without being affected by the rotation operation of the pulse wave detection sensor 30 caused by the rotation driving section 31.

Therefore, the pressure pulse wave can be accurately detected. Since the plurality of guide pins 27 exist, the guiding function can be sufficiently maintained even in the case where the weight of the portions (the rotation driving section 31 and the pulse wave detection sensor 30) which are supported by the pressing member 32 is large.

According to the pulse wave detector 10, in the hole portions of the housing 20 into which the two guide pins 27 (27A, 27B) of the four guide pins 27 are fitted, the guide pins 27 are fitted more tightly than in the hole portions into which the guide pins 27 (27C, 27D) that are of the four guide pins 27, and that are other than the guide pins 27A, 27B are fitted.

The guide pins 27 which are loose-fitted to the housing 20, and the two guide pins 27 which are tightly fitted to the housing 20 exist as described above. Even in the case where a production error occurs in the housing 20 or the pressing member 32, the error can be absorbed by the guide pins 27 which are loose-fitted, while realizing the function of guiding the movement of the pressing member 32.

In the pulse wave detector 10, at least one of the guide pins 27A and 27B shown in FIG. 5 may be omitted. Even in such a configuration, when the pressing member 32 is moved along the guide pins 27C and 27D, the pulse wave detection sensor 30 can be pressed against the body surface at a stabilized pressure.

The pulse wave detector 10 may have a configuration where, similarly with the guide pins 27C and 27D, the guide pin 27A or 27B is press-fitted into the hole portions 251 and 261 of the housing 20.

When the pulse wave detector 10 has three or more guide pins 27 including: at least one guide pin 27 (the second guiding member) which is loose-fitted into the hole portion of the housing 20; and at least two guide pins 27 (the first guiding members) which are press-fitted into the hole portions of the housing 20, namely, it is possible to achieve the effect of absorbing the above-described error.

The number of the guide pins 27 may be five or more. When the configuration where four guide pins 27 are disposed as shown in FIG. 5 is employed, both the effect of reduction of the production cost of the pulse wave detector 10, and that of improvement of the accuracy of the detection of a pressure pulse wave are attained.

The placement positions of the guide pins 27 which are placed around the pulse wave detection sensor 30 are not required to be the four corners in the case where the plan-view shape of the detection surface 37 of the pulse wave detection sensor 30 is rectangular as shown in FIG. 5.

Figure 6A:
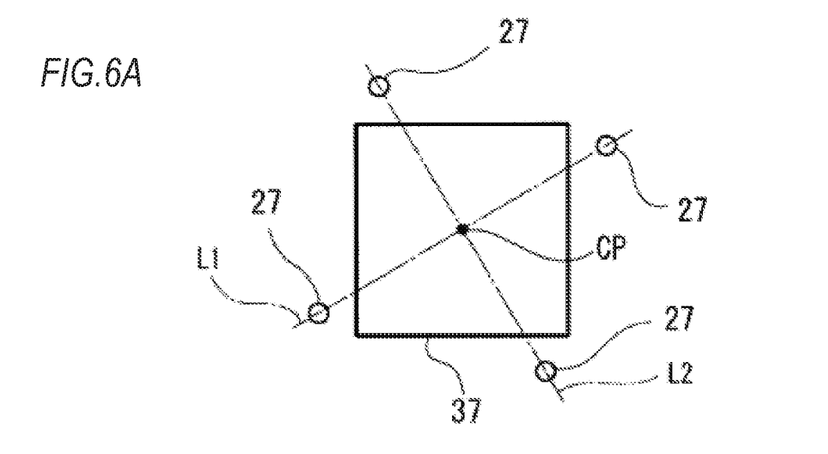
FIGS. 6A to 6C are plan views each showing a modification of the arrangement of guide pins 27 of the pulse wave detector 10 shown in FIG. 1.
Figure 6B:
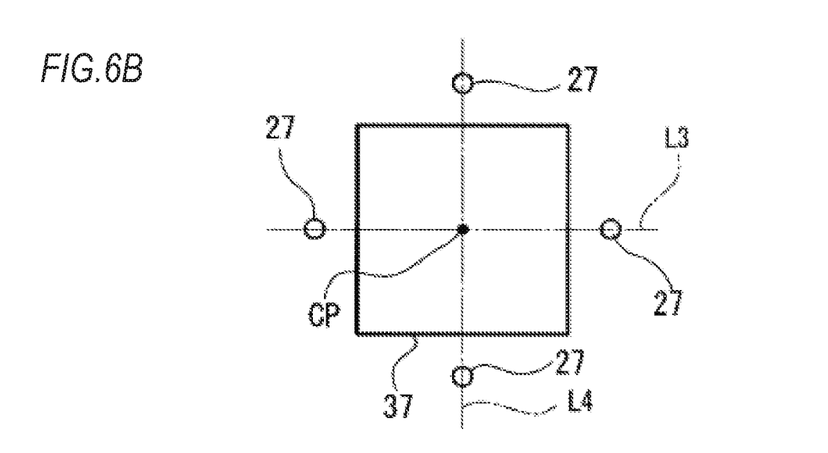
Figure 6C:
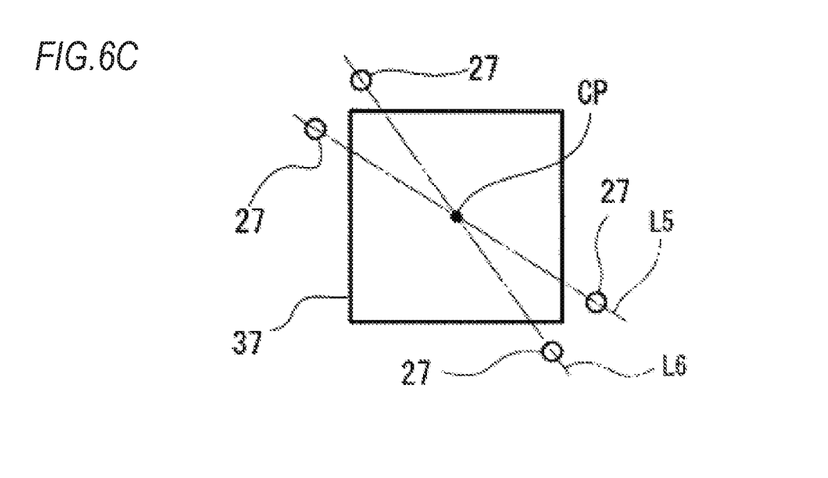

For example, the four guide pins 27 may be placed around the detection surface 37 of the pulse wave detection sensor 30 as shown in FIGS. 6A to 6C.

All of the configurations shown in FIGS. 6A to 6C have two pairs of guide pins 27 in each of which the guide pins are placed on a straight line (straight lines L1 to L6 in FIG. 6) passing through the center CP of the detection surface 37 of the pulse wave detection sensor 30 and across the pulse wave detection sensor 30.

According to the configurations, the center CP of the detection surface 37 can be aligned with the center of a rectangle which is formed by connecting the four guide pins 27. The center of the rectangle which is formed by connecting the four guide pins 27 is a place which is most stable in the pressing member 32. Since the center CP of the detection surface 37 exists below the place, the detection surface 37 of the pulse wave detection sensor 30 can be pressed against the body surface at a stabilized pressure.

Although, in the example shown in FIG. 5, the guide pins 27A and 27B which are arranged on the diagonal line of the rectangular detection surface 37 are relatively loose-fitted into the housing 20, the positions of the guide pins 27 which are loose-fitted into the housing 20 are not limited to those shown in FIG. 5.

Figure 7:
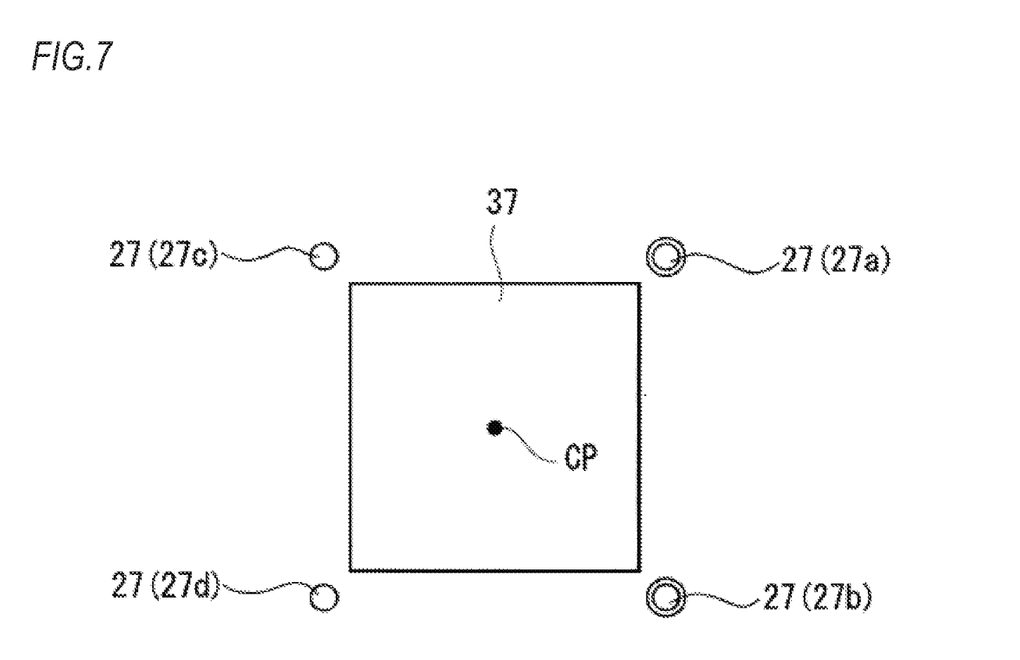
FIG. 7 is a plan view diagrammatically showing a modification of a fitted state of the guide pins 27 and housing 20 of the pulse wave detector 10 shown in FIG. 1.

As shown in FIG. 7, for example, a configuration may be possible where guide pins 27a and 27b which are arranged along one side of the rectangular detection surface 37 are loose-fitted into the housing 20, and guide pins 27c and 27d which are arranged along a side of the detection surface 37 that is parallel to the one side are press-fitted into the housing 20.

Figure 8:
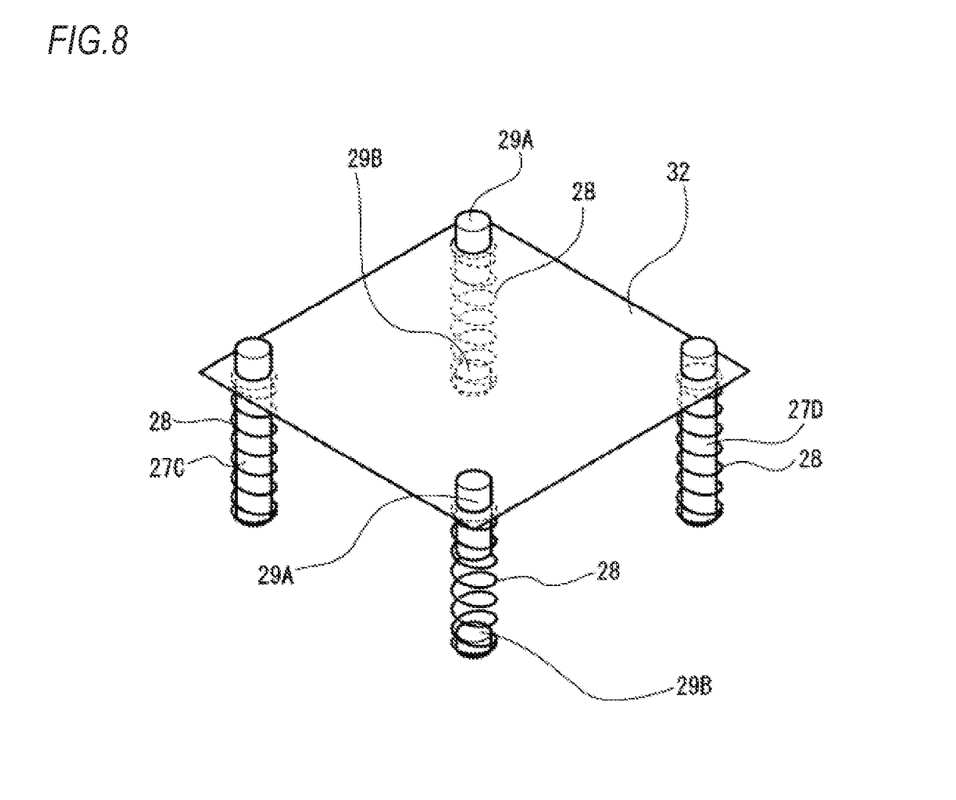
FIG. 8 is a perspective view diagrammatically showing a modification of the pulse wave detector 10 shown in FIG. 1.

FIG. 8 is a diagram showing a modification of the pulse wave detector 10 shown in FIG. 1.

The pulse wave detector of the modification shown in FIG. 8 has a configuration where a pair of spring locking protrusions 29A and 29B are disposed in place of the guide pins 27A and 27B of the pulse wave detector 10.

The spring locking protrusions 29B are disposed on the lower end portion 26 of the housing 20. The spring locking protrusions 29A are disposed on portions of the pressing member 32 which are opposed to the corresponding spring locking protrusions 29B. One ends of the springs 28 are fixed to the spring locking protrusions 29A, and the other ends of the springs 28 are fixed to the spring locking protrusions 29B.

Even in the configuration where only two guide pins 27 are used as described above, the pressing member 32 can be moved in the direction Z by a stabilized force, and the accuracy of the detection of a pulse wave can be improved.

The above-disclosed embodiment should be considered in all respects to be illustrative and not restrictive. The scope of the present invention is represented by the appended claims rather than the foregoing description, and all changes within the meaning and range of equivalents thereof are intended to be covered therein.

As described above, the following matters are disclosed in the specification.

The disclosed pulse wave detector includes: a pulse wave detection sensor which is configured to detect a pressure pulse wave from an artery of a measurement subject; a pressing member which supports the pulse wave detection sensor and is configured to be moved in one direction to press the pulse wave detection sensor against a body surface of the measurement subject; a plurality of guiding members which are placed around the pulse wave detection sensor in a plan view as seen in the one direction and extend in the one direction; and a supporting member which supports the plurality of guiding members, wherein the pressing member includes pass-through portions through which the plurality of guiding members are passed to be movable along the guiding members, respectively.

In the disclosed pulse wave detector, the plurality of guiding members include at least one pair of guiding members which are arranged across a detection surface of the pulse wave detection sensor in the plan view.

In the disclosed pulse wave detector, a center of gravity or a center of the detection surface of the pulse wave detection sensor is located on a straight line connecting the pair of guiding members in the plan view.

In the disclosed pulse wave detector, the pair of the guiding members are provided two pairs.

In the disclosed pulse wave detector, the guiding members are provided three or more, the supporting member which supports the guiding members has fitting portions into which end portions in the one direction of the guiding members are fitted, the three or more guiding members include at least two first guiding members and at least one second guiding member, and in the fitting portions into which the first guiding members are fitted, the guiding members are fitted more tightly than in the fitting portion into which the second guiding member is fitted.

In the disclosed pulse wave detector, the guiding members are rod-like members, and the pulse wave detector further includes springs through which the guiding members are passed, and which are placed between the pressing member and the pulse wave detection sensor.

The disclosed pulse wave detector further includes a rotating mechanism which is configured to rotate a detection surface of the pulse wave detection sensor about each of two directions that are perpendicular to the one direction, The disclosed biometric information measurement device includes: the above pulse wave detector; and a biometric information calculating section which is configured to calculate biometric information based on the pulse wave detected by the pulse wave detection sensor.

Accordingly, it is possible to provide a pulse wave detector in which a pulse wave detection sensor can be pressed against the body surface at a stabilized pressure, and also a biological information measurement device including the detector.

The present invention is convenient and effective particularly in application to a blood pressure monitor or the like.

Although the present invention has been described with reference to the specific embodiment, the present invention is not limited to the embodiment, and various changes can be made without departing from the technical concept of the disclosed invention.

The invention claimed is:
1. A pulse wave detector comprising:
a pulse wave detection sensor which is configured to detect a pressure pulse wave from an artery of a measurement subject;
a pressing member which supports the pulse wave detection sensor and is configured to be moved in one direction to press the pulse wave detection sensor against a body surface of the measurement subject;
a plurality of guiding members which are placed around the pulse wave detection sensor in a plan view as seen in the one direction and extend in the one direction;
a housing which supports the plurality of guiding members; and
a first actuator which is configured to move the pressing member with respect to the housing, wherein the pressing member includes pass-through portions, the housing has fitting portions into which end portions in the one direction of the guiding members are fitted, and the plurality of guiding members are passed through the pass-through portions, and the pressing member is movable along the guiding members respectively.

2. The pulse wave detector according to claim 1, wherein the plurality of guiding members includes at least one pair of guiding members which are arranged across a detection surface of the pulse wave detection sensor in the plan view.

3. The pulse wave detector according to claim 2, wherein a center of gravity or a center of the detection surface of the pulse wave detection sensor is located on a straight line connecting the pair of guiding members in the plan view.

4. The pulse wave detector according to claim 2, wherein the at least one pair of guiding members comprises two pairs.

5. The pulse wave detector according to claim 1, wherein the plurality of guiding members comprises three or more guide-members, the three or more guiding members include at least two first guiding members and at least one second guiding member, and in the fitting portions into which the first guiding members are fitted, the guiding members are fitted more tightly than in the fitting portion into which the second guiding member is fitted.

6. The pulse wave detector according to claim 1, wherein the pulse wave detector further comprising:

springs through which the guiding members are passed, and which are placed between the pressing member and the pulse wave detection sensor.

7. The pulse wave detector according to claim 1, further comprising:

a rotating mechanism which is configured to rotate a detection surface of the pulse wave detection sensor about each of two directions that are perpendicular to the one direction, and a second actuator which drives the rotating mechanism.

8. A biometric information measurement device comprising:

the pulse wave detector according to claim 1; and a biometric information calculating section which is configured to calculate biometric information based on the pulse wave detected by the pulse wave detection sensor.

* * * * *